(12) United States Patent
Li et al.

(10) Patent No.: US 10,481,062 B2
(45) Date of Patent: Nov. 19, 2019

(54) METHOD FOR IMPROVING IDENTIFICATION DEGREE OF LOW-LUMINOSITY DISPERSED-PHASE PARTICLES IN MULTIPHASE SYSTEM

(71) Applicant: INSTITUTE OF PROCESS ENGINEERING, CHINESE ACADEMY OF SCIENCES, Beijing (CN)

(72) Inventors: Xiangyang Li, Beijing (CN); Chao Yang, Beijing (CN); Yiting Xiao, Beijing (CN); Zaisha Mao, Beijing (CN)

(73) Assignee: INSTITUTE OF PROCESS ENGINEERING, CHINESE ACADEMY OF SCIENCES (CN)

( * ) Notice: Subject to any disclaimer, the term of this patent is extended or adjusted under 35 U.S.C. 154(b) by 0 days.

(21) Appl. No.: 16/026,154

(22) Filed: Jul. 3, 2018

(65) Prior Publication Data
US 2019/0011346 A1    Jan. 10, 2019

(30) Foreign Application Priority Data

Jul. 7, 2017   (CN) .......................... 2017 1 0551182

(51) Int. Cl.
*G01N 15/02*     (2006.01)
*G01N 15/00*     (2006.01)

(52) U.S. Cl.
CPC . *G01N 15/0227* (2013.01); *G01N 2015/0003* (2013.01)

(58) Field of Classification Search
CPC ....... G01N 15/0227; G01N 2015/0003; G01N 15/00; D06F 93/005; G06K 17/0022; G06K 19/027; G06K 19/06028; G06Q 10/08
USPC .................................................. 356/300–343
See application file for complete search history.

(56) References Cited

U.S. PATENT DOCUMENTS 6,831,741 B1 * 12/2004 De Kruif ............. G01N 21/474
356/338

* cited by examiner

Primary Examiner — Tri T Ton
(74) Attorney, Agent, or Firm — McDonald Hopkins LLC

(57) ABSTRACT

The present invention provides a method for improving an identification degree of low-luminosity dispersed-phase particles in a multiphase system. The method comprises: adding additive particles into a multiphase system containing low-luminosity dispersed-phase particles before photographing the multiphase system to obtain an image including the low-luminosity dispersed-phase particles, wherein the refractivity of the additive particles is greater than that of the low-luminosity dispersed-phase particles. The method can enhance the luminosity of the continuous phase in the multiphase system, thereby causing a large gray difference between the continuous phase and the dispersed-phase particles, improving the identification degree of the low-luminosity dispersed-phase particles in the image for conducting accurate identification by image analysis software and further being capable of accurately measuring needed parameters such as particle size, concentration or speed and the like of the dispersed-phase particles in a multiphase reactor.

15 Claims, 12 Drawing Sheets

METHOD FOR IMPROVING IDENTIFICATION DEGREE OF LOW-LUMINOSITY DISPERSED-PHASE PARTICLES IN MULTIPHASE SYSTEM

CROSS-REFERENCE TO RELATED APPLICATIONS

This application claims priority to Chinese Patent Application No. 201710551182.5, filed on Jul. 7, 2017, the contents of which are incorporated herein in its entirety by reference.

TECHNICAL FIELD

The present invention belongs to the technical field of physical measurement and relates to a method for improving an identification degree of low-luminosity dispersed-phase particles in a multiphase system.

BACKGROUND

An industrial reactor often contains one, two, and even more than two dispersed phases, and the distribution of dispersed-phase particles in the reactor is an important reflection of the performance of the reactor and is also an important basis of the design and amplification of the reactor.

In an invasive photogrammetric technology developed in recent years, a measuring instrument (probe) with a photographing function extends into the reactor directly to conduct online photographing on multiphase fluid that moves at high speed at a measured point, and image processing software is utilized for identifying, processing and counting the dispersed-phase particles, thereby obtaining concentration and particle-size distribution of the dispersed-phase particles at the measured point. The method is intuitive and accurate. Currently, this kind of technology mainly includes an optical photographing probe technology from German SOPAT Company, a PVM (Particle Video Microscope) technology from American Mettler Toledo Company and a multiphase measuring instrument based on a telecentric photographing principle from Institute of Process Engineering, Chinese Academy of Sciences. In the invasive photographing technology, the difference of gray values of all phase states of medium images in a picture is a core problem for accurately identifying all phases and further obtaining accurate measurement results. According to an imaging principle of a camera, light reflected from a surface of a scenery converges on a photosensitive region of a film or an image sensor by a lens to form a latent image, and gray of the latent image depends on lighting conditions (intensity, colors and irradiating directions) and surface properties (colors, shapes and roughness and the like) of a photographed object. Under common photographing conditions (fixed light intensity and color, and front irradiation), reflection of the continuous phase (usually water solution) in the multiphase system to light rays is weak, and luminosity is low, so the gray value of the latent image is small. In this way, the stronger the reflection of the dispersed phase particles to the light rays is, the higher the luminosity is and the larger the gray value of the latent image is, so the dispersed-phase particles are in sharp contrast with the continuous phase in the picture and can be easily and accurately identified and processed by the image processing software. This is a basis of successful application of the invasive photographing technology.

While in actual measurement, the dispersed-phase particles in many systems are low-luminosity dark solid particles or/and bubbles. At the moment, gray values of the latent images of the continuous phase and the dispersed phase in the picture are lower and an obvious gray difference cannot be formed, so that an identification degree of all the phases in the picture is poor and all phases of media cannot be identified and processed by the image processing software. A more direct method is to increase the intensity of illumination, but with a purpose of reducing invasive errors as many as possible, it is impossible to install more LED lamps or illuminating optical fibers on the invasive photographing probe. In addition, over-high illuminating intensity can also cause internal heating, so the problem is hard to solve by increasing the illuminating intensity. In a common method for actual measurement, a reflecting board or backside illumination is added at an opposed side of the measured point in front of the probe, and by change of an illuminating environment of the measured region, the gray value of the latent image of the continuous phase on the picture is greatly increased, the gray value of the dispersed-phase particles is greatly reduced and a strong contrast is formed on the picture, thereby achieving identification of the two phases. However, discovered from practices, the addition of the reflecting board can cause a larger invasive error, and especially when a direction of an incoming flow at the measured point and the probe form an included angle of 180 degrees, the reflecting board blocks the incoming flow, causing serious measurement errors.

Mie scattering theory is based on the interaction of electromagnetic waves and charges that form substances. A particle group composed of many molecules is used as a multistage subgroup and is excited by incident waves to form a vibratory multistage subgroup which then radiates secondary wavelets outwards. Theoretically, amplitudes of all stages of wavelets are convergent series, and a sum of squares of the series in a specific direction is scattering light intensity in this direction.

SUMMARY

For defects in the prior art, the purpose of the present invention is to provide a method for improving an identification degree of low-luminosity dispersed-phase particles in a multiphase system. The method can enhance the luminosity of the continuous phase in the multiphase system, thereby causing a large gray difference between the continuous phase and the dispersed-phase particles, improving the identification degree of the low-luminosity dispersed-phase particles in the image for conducting accurate identification by image analysis software and further being capable of accurately measuring needed parameters such as particle size, concentration or speed and the like of the low-luminosity dispersed-phase particles in a multiphase reactor.

The low-luminosity dispersed-phase particles are particles with a refractivity (the refractivity is actually a complex number, a real part is a refraction coefficient and an imaginary part is an absorption coefficient) that meets the following conditions: the real part is less than 1.5, such as 1.4, 1.3, 1.2, 1.0, 0.8, 0.5 or 0.3, and the imaginary part is more than 0.5, such as 0.6, 0.8, 1.0, 1.2, 1.5, 1.8 or 2.5 and the like.

In order to achieve the purpose, the present invention adopts the following technical solution:

A method for improving an identification degree of low-luminosity dispersed-phase particles in a multiphase system is provided. The method comprises adding additive particles into a multiphase system containing low-luminosity dispersed-phase particles before photographing the multiphase system to obtain an image including the low-luminosity dispersed-phase particles, wherein the refractivity of the additive particles is greater than that of the low-luminosity dispersed-phase particles.

In the present invention, proper additive particles are added into the multiphase system, so that the luminosity of the continuous phase in the multiphase system is greatly increased. Then by photographing the multiphase system, an obvious gray difference between the continuous phase and the dispersed-phase particles on an image can be caused and the luminosity range of a measuring system is in a tolerance range of a photosensitive element, thereby improving the identification degree of the low-luminosity dispersed-phase particles in the image.

By replacement of an existing reflecting board with the additive particles, a problem that the reflecting board interferes with a flow field is effectively solved and measurement errors are greatly reduced.

As a preferred technical solution, the method further comprises: carrying out analysis processing on the image of the low-luminosity dispersed-phase particles to obtain parameters such as particle size, concentration or speed of the dispersed-phase particles in the multiphase system. Those skilled in the art can also process the image of the low-luminosity dispersed-phase particles according to actual needs so as to acquire other information of the dispersed phase or the multiphase system.

The refractivity of the additive particles should be greater than that of the low-luminosity dispersed-phase particles. For example, the refractivity of the additive particles is 1.1, 1.3, 1.5, 1.8, 2.1, 2.3, 2.5, 3.1, 3.5, 3.8, 4.0, 4.5, 5.2 or 6.8 times that of the low-luminosity dispersed-phase particles, and preferably is 2.0 times or greater.

The concentration of the additive particles in the multiphase system is 5 mg/L-7 mg/L, such as 5.1 mg/L, 5.2 mg/L, 5.3 mg/L, 5.5 mg/L, 5.8 mg/L, 6.2 mg/L, 6.5 mg/L, 6.8 mg/L or 6.9 mg/L and the like. In this concentration range, the addition of the additive particles has almost no influence on physical properties of the multiphase system.

The particle size of the additive particles is 100 nm-10 μm, such as 150 nm, 200 nm, 230 nm, 280 nm, 310 nm, 400 nm, 500 nm, 800 nm, 900 nm, 1 μm, 3 μm, 5 μm, 8 μm or 9 μm and the like. If the particle size of the additive particles is in this range, noisy points are prevented from being formed on the image and interfering with the identification of the low-luminosity dispersed-phase particles in the image on a basis of guaranteeing that the low-luminosity particles can be identified by the image processing software, and the interference on the flow field of the multiphase system is low.

The color of the additive particles belongs to a bright color system, namely a color with high luminosity, such as white, bright red, bright orange, golden yellow, jade green, pink blue or light purple and the like, and preferably is white. The selected white additive particles have an advantage of low absorption coefficient and can reflect various wavelengths of visible lights without difference for the wavelength ranges of the LED lamps used for photographing.

The additive particles are particles with a scattering angle of 90-270 degrees calculated according to the Mie scattering theory, such as particles with a scattering angle of 95 degrees, 100 degrees, 102 degrees, 105 degrees, 110 degrees, 120 degrees, 150 degrees, 180 degrees, 190 degrees, 200 degrees, 210 degrees, 230 degrees or 260 degrees and the like.

Preferably, the additive particles are selected from any one or a combination of at least two of titanium dioxide particles, silicon dioxide particles or aluminum oxide particles. Typical but non-restrictive combinations are exemplified as titanium dioxide particles and silicon dioxide particles, titanium dioxide particles and aluminum oxide particles, titanium dioxide particles, silicon dioxide particles and aluminum oxide particles.

The concentration of the low-luminosity dispersed-phase particles in the multiphase system is 50 wt % or less, such as 2 wt %, 5 wt %, 8 wt %, 10 wt %, 13 wt %, 15 wt %, 18 wt %, 21 wt %, 28 wt %, 30 wt %, 35 wt %, 40 wt % or 48 wt % and the like. The wt % means weight percentage content.

The low-luminosity dispersed-phase particles are selected from bubbles and/or solid particles.

The method is applicable to immersive photographing or other forms of photographing, and preferably the immersive photographing. The immersive photographing means photographing in the multiphase system, and for example, an immersive multiphase measuring instrument is placed in the multiphase system for photographing.

Preferably, an immersive online multiphase measuring instrument is used for photographing the low-luminosity dispersed-phase particles in the multiphase system, and a gas-liquid multiphase system or a liquid-solid multiphase system is preferred as the multiphase system.

As a preferred technical solution, the method comprises the following steps: adding white additive particles with a scattering angle of 90-270 degrees calculated according to the Mie scattering theory to the multiphase system containing the low-luminosity dispersed-phase particles before carrying out immersive photographing on the multiphase system to obtain an image including the low-luminosity dispersed-phase particles, wherein the refractivity of the additive particles is 2.0 times or greater that of the low-luminosity dispersed-phase particles, the concentration of the additive particles in the multiphase system is 5 mg/L-7 mg/L, the particle size of the additive particles is 100 nm-10 μm, and the concentration of the low-luminosity dispersed-phase particles in the multiphase system is 50 wt % or less.

The immersive online multiphase measuring instrument is used for photographing the dispersed-phase particles in the multiphase system. The immersive online multiphase measuring instrument can be selected as the immersive online multiphase measuring instrument disclosed in CN 105928841A, including:

a packaging pipe;

a window connected to one end of the packaging pipe in a sealing manner;

an illuminating system for illuminating a multiphase flow, including LED lamps and a modulating light source connected with the LED lamps, wherein the modulating light source includes a power supply, a signal generator and an oscilloscope;

a photographic system for photographing, including a telecentric lens and an image sensor;

a controller connected with the signal generator and the image sensor;

a signal processing and output system connected with the image sensor; and a display system connected with the signal processing and output system, wherein the LED lamps, the telecentric lens and the image sensor are positioned in the packaging pipe, and the controller controls the exposure period of the image sensor to be shorter than the pulse period of the signal generator.

Methods disclosed in CN 105928847A and CN 105738648A can be respectively referred for the method that utilizes the immersive online multiphase measuring instrument to measure the concentration, the particle size and the speed of the dispersed-phase particles in the multiphase system.

Numerical ranges of the present invention not only include point values listed above, but also include any point value without being listed between the numerical ranges. Considering length and simplicity, the present invention does not list specific point values included in the ranges any more.

Compared with the prior art, the present invention has the beneficial effects that:

According to the method for improving the identification degree of the low-luminosity dispersed-phase particles in the multiphase system provided in the present invention, under the premise of almost not changing the physical properties of the multiphase system, large measurement error caused by the existing method (for example, the reflecting board is added or a back illuminating device is provided in the multiphase system) is avoided by increasing the luminosity of the continuous phase and greatly increasing the gray difference between the continuous phase and the low-luminosity dispersed-phase to a degree that the image analysis software can conduct identification easily and accurately. The measurement error of the method is less than 5%, and the problem that the multiphase system that adopts the low-luminosity particles as the dispersed phase is difficult to be photographed to further obtain related information (parameters such as particle size, concentration or speed of the low-luminosity dispersed-phase particles) is effectively solved.

The method for improving the identification degree of the low-luminosity dispersed-phase particles in the multiphase system is applicable to various photographing apparatuses.

In the figure: 1. window; 2. LED lamp; 3. stainless-steel packaging pipe; 4. telecentric lens; 5. miniature high-speed CMOS camera; 6. modulating light source; 7. wire; 8. USB3.0 data transmission line; 9. high-speed image acquisition card; and 10. sampling computer.

Figure 2:
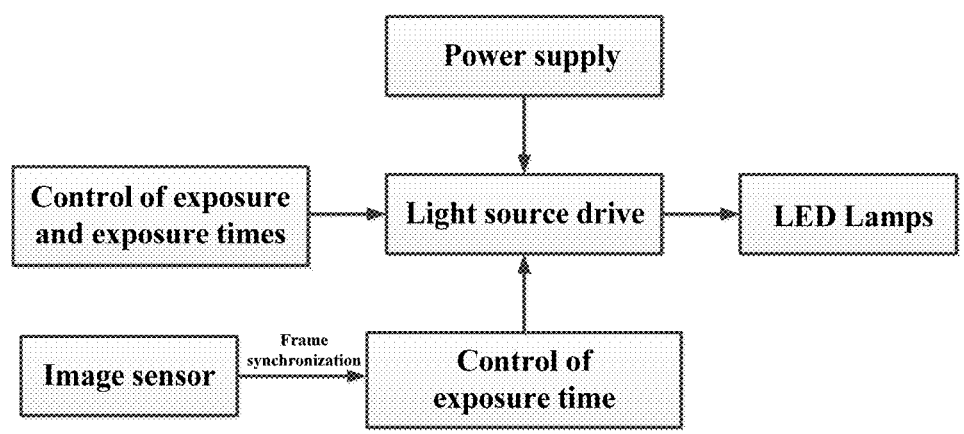
Figure 3:
Figure 4:
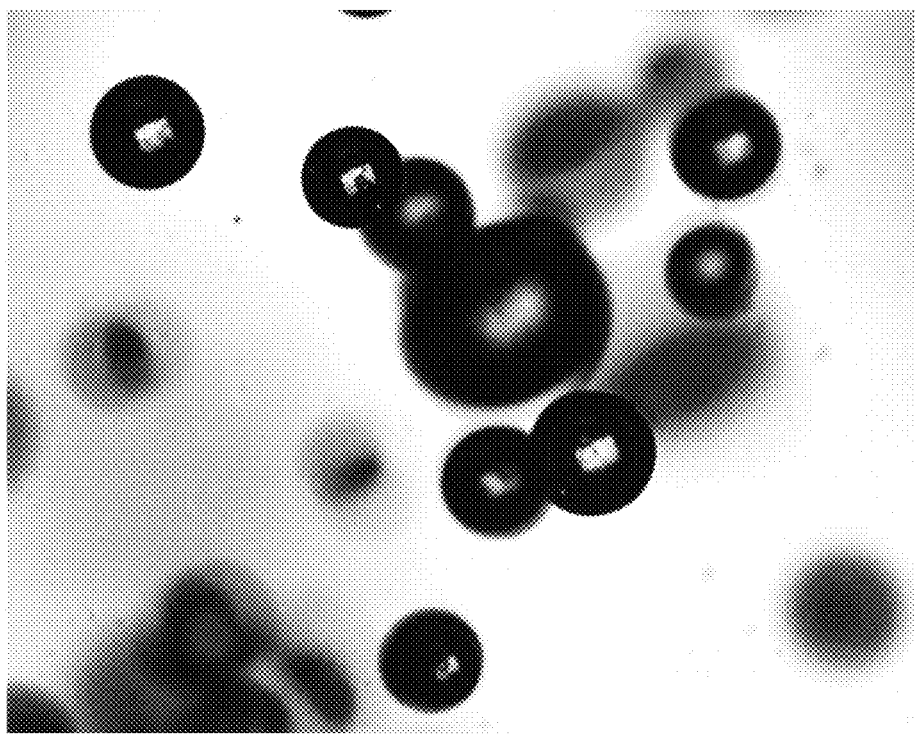
Figure 5:
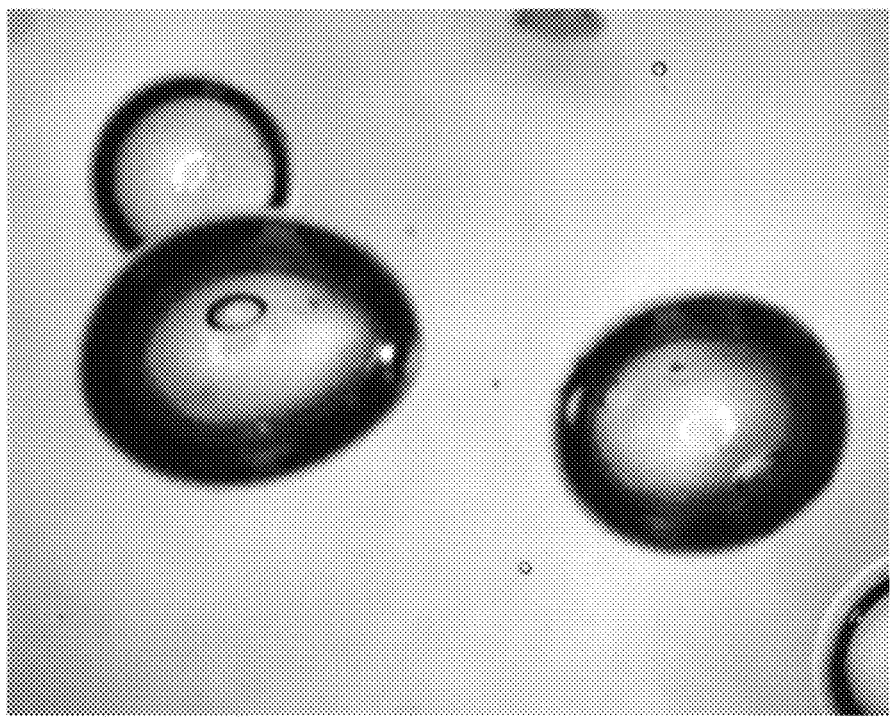
Figure 6:
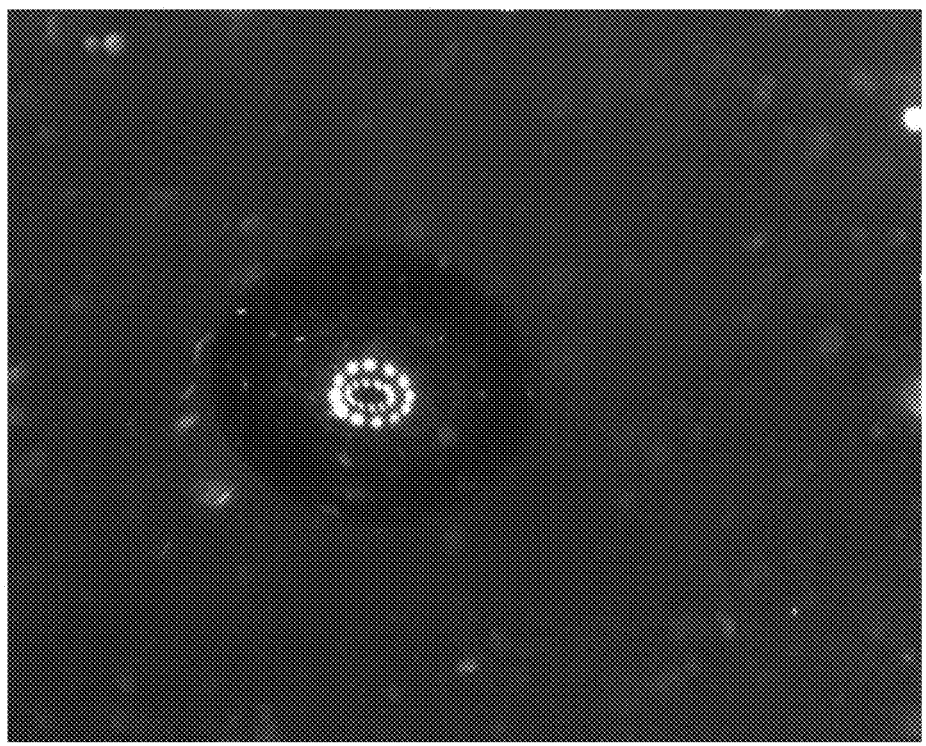
Figure 7:
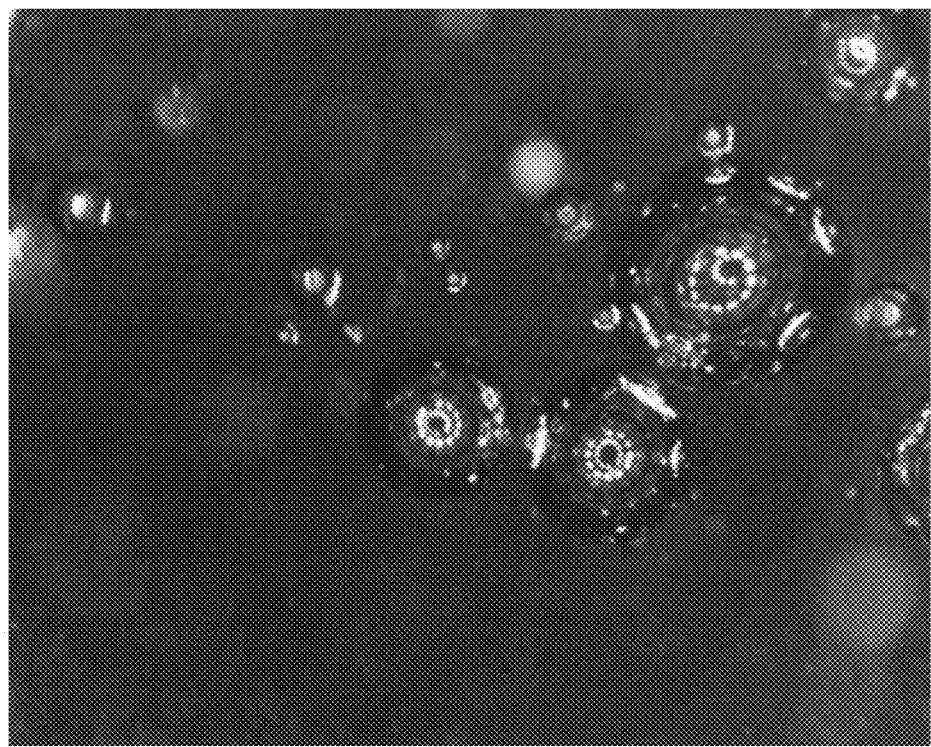
Figure 8:
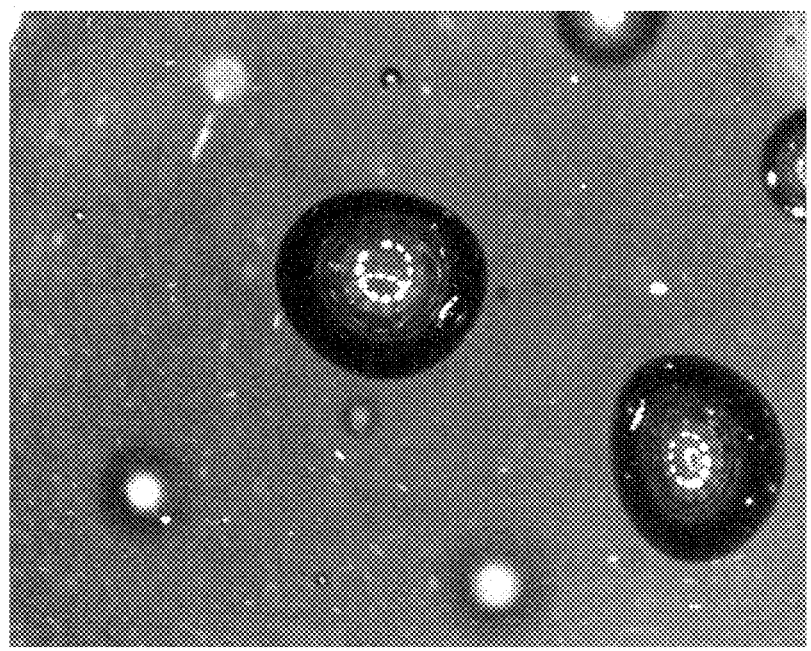
Figure 9A:
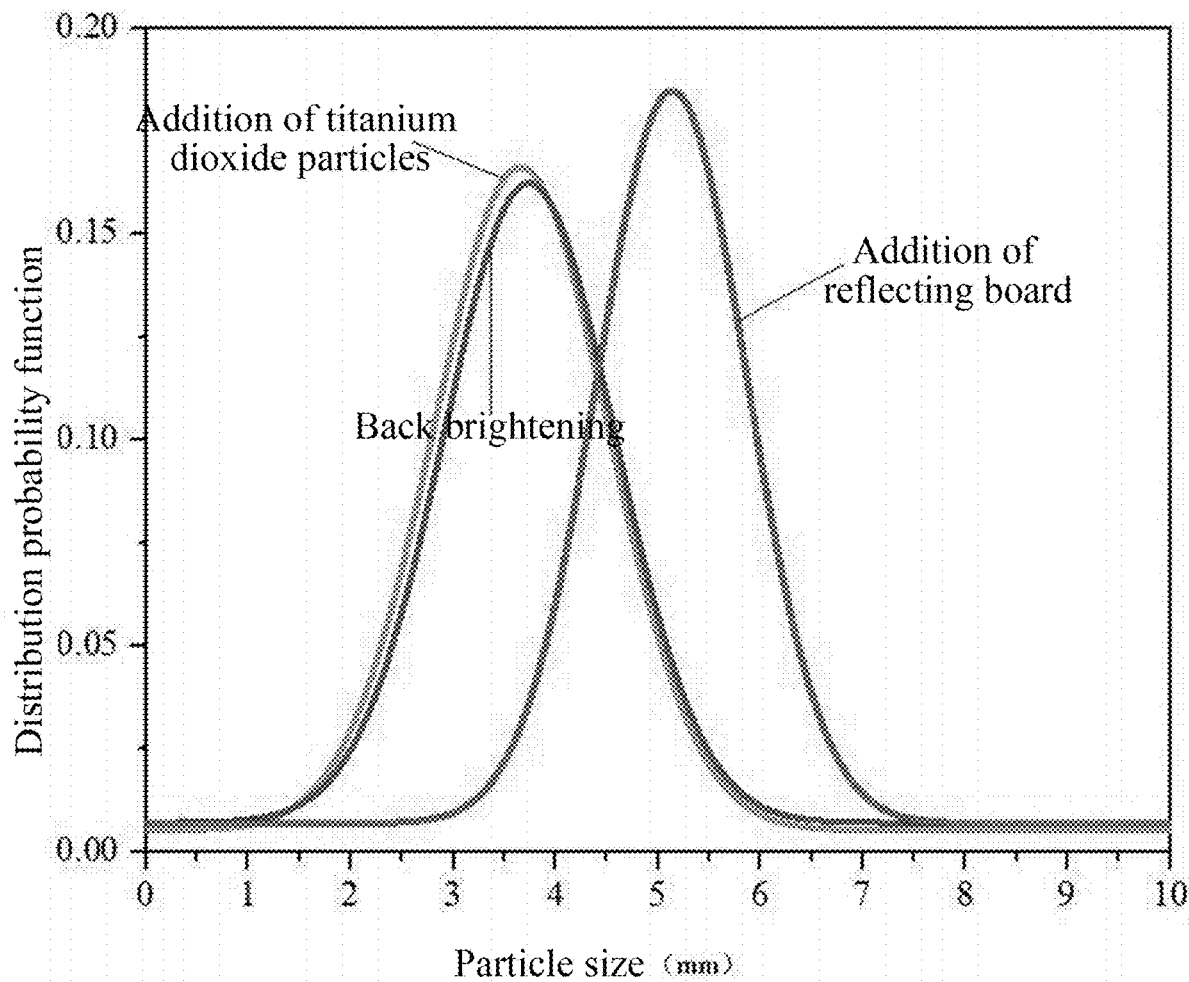
Figure 9B:
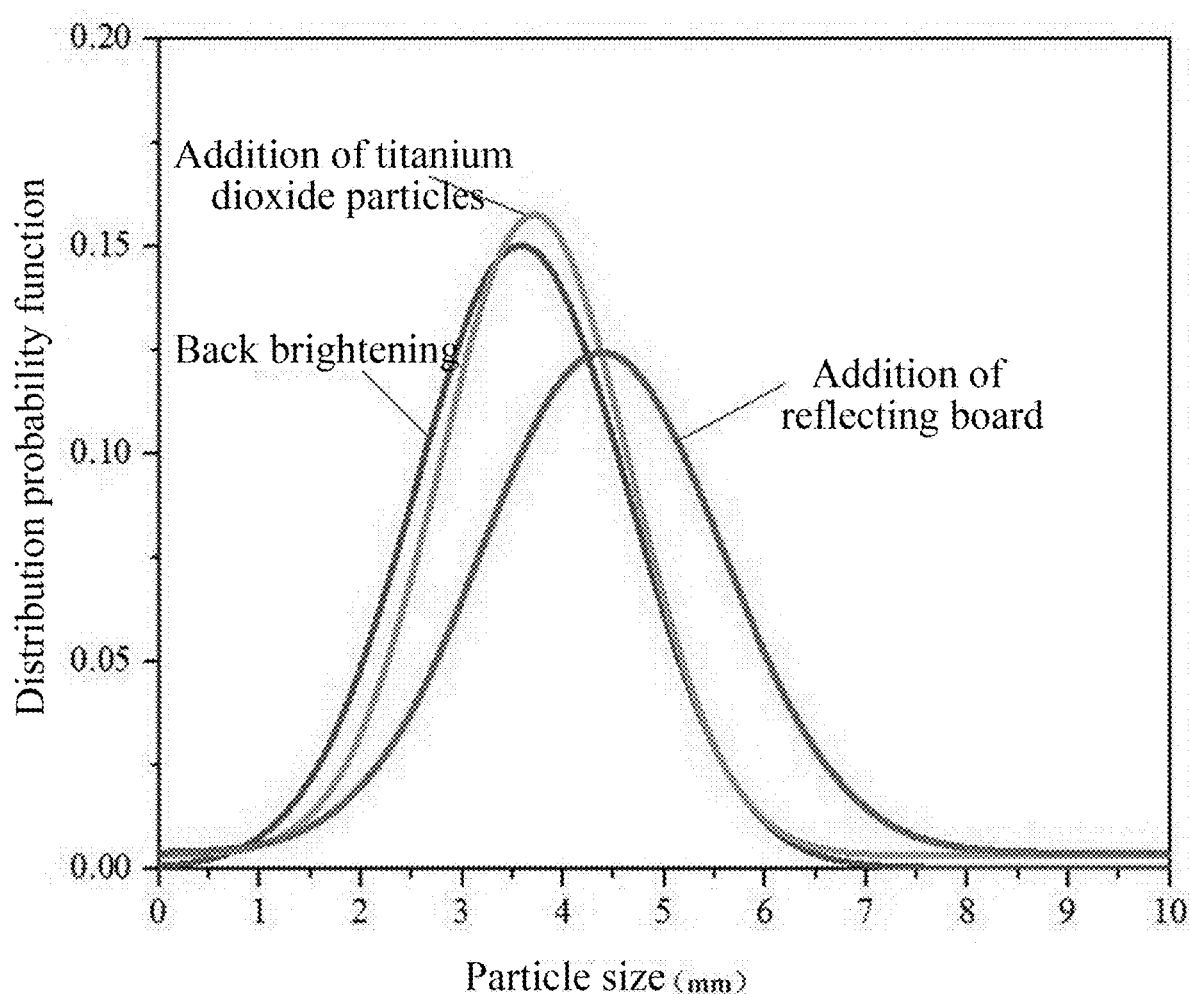
Figure 9C:
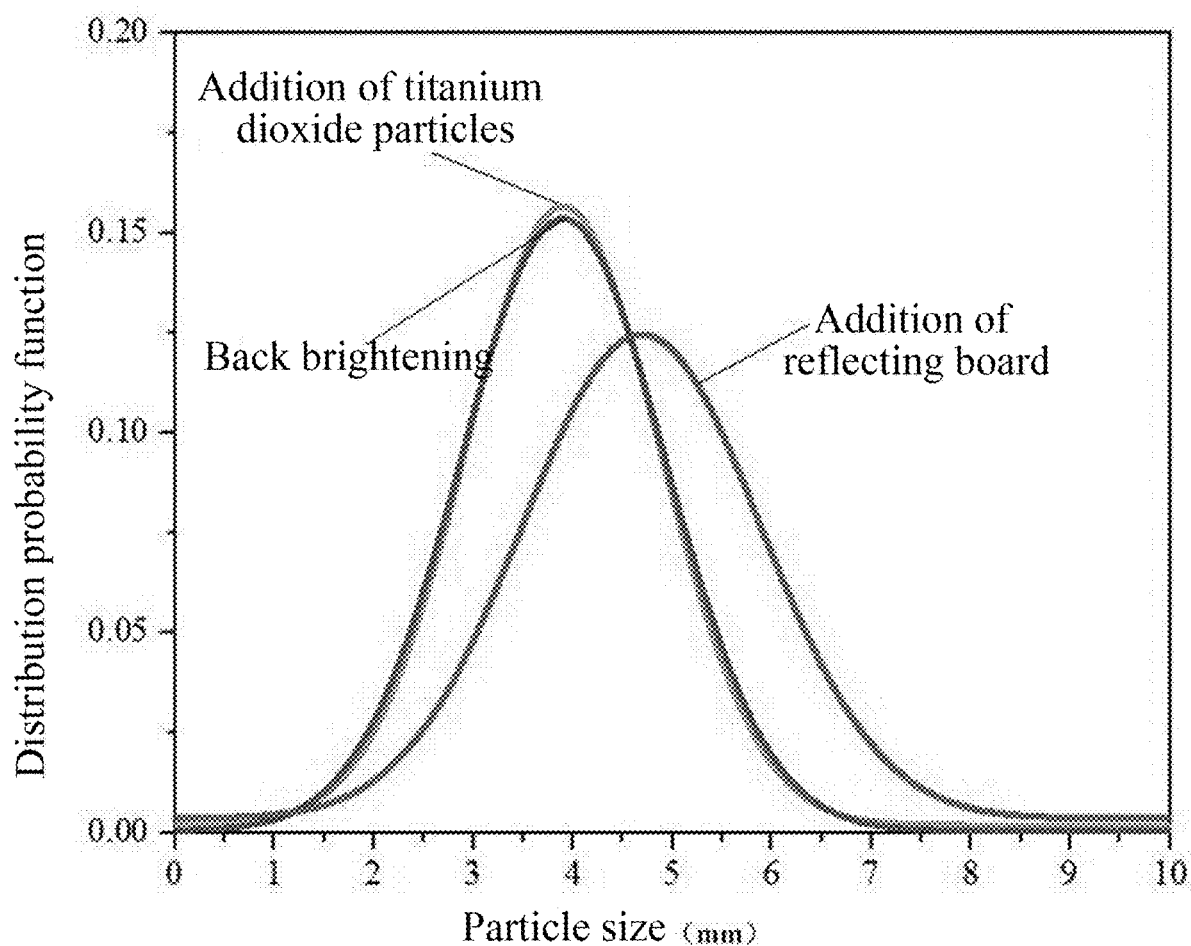
Figure 9D:
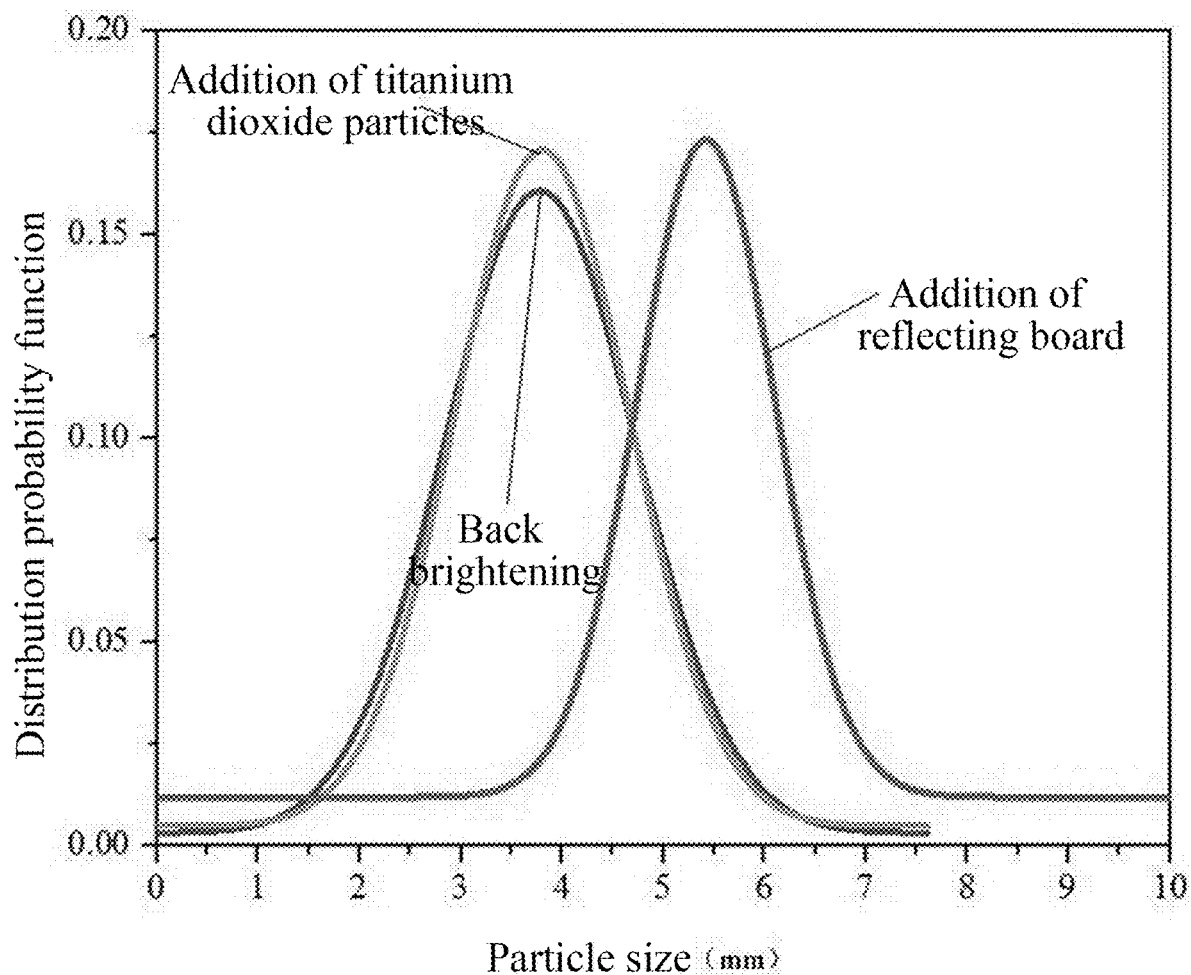

FIG. 2 is a schematic diagram illustrating a control mode provided by Example 1;

FIG. 3 is an image illustrating a gas-liquid system obtained through illumination of an immersive probe and a same-direction light source (i.e., an illuminating system in an immersive online multiphase measuring instrument) in Example 1;

FIG. 4 is an image illustrating a gas-liquid system obtained through illustration of an immersive probe and the backside light source (i.e., back illustration outside a reactor) in Example 1;

FIG. 5 is an image illustrating a gas-liquid system obtained by adopting an immersive probe and adding a reflecting board on the back (i.e., the reflecting board is connected with the probe by two thin and long supporting feet, and fluid to be measured flows through a gap between the two supporting feet) in Example 1;

FIG. 6 is an image illustrating a gas-liquid system obtained by adopting an immersive probe and adding silicon dioxide particles in Example 1;

FIG. 7 is an image illustrating a gas-liquid system obtained by adopting an immersive probe and adding aluminum oxide particles in Example 1;

FIG. 8 is an image illustrating a gas-liquid system obtained by adopting an immersive probe and adding titanium dioxide particles in Example 1;

FIG. 9a is a comparison diagram illustrating bubble size distributions in contrast experiments under the conditions of addition of titanium dioxide, addition of reflecting board and back brightening provided by (1) in Example 3;

FIG. 9b is a comparison diagram illustrating bubble size distributions in contrast experiments under the conditions of addition of titanium dioxide, addition of reflecting board and back brightening provided by (2) in Example 3;

FIG. 9c is a comparison diagram illustrating bubble size distributions in contrast experiments under the conditions of addition of titanium dioxide, addition of reflecting board and back brightening provided by (3) in Example 3; and FIG. 9d is a comparison diagram illustrating bubble size distributions in contrast experiments under the conditions of addition of titanium dioxide, addition of reflecting board and back brightening provided by (4) in Example 3.

DETAILED DESCRIPTION

The technical solution of the present invention is further described in combination with drawings and specific embodiments.

A method for improving an identification degree of low-luminosity dispersed-phase particles in a multiphase system comprises: white additive particles with a scattering angle of 90-270 degrees calculated according to Mie scattering theory are added into a multiphase system containing low-luminosity dispersed-phase particles before immersive photographing is carried out on the multiphase system to obtain an image including the low-luminosity dispersed-phase particles, wherein the refractivity of the additive particles is 2.0 times or greater that of the low-luminosity dispersed-phase particles; the concentration of the additive particles in the multiphase system is 5 mg/L-7 mg/L; the particle size of the additive particles is 100 nm-10 µm; and the concentration of the low-luminosity dispersed-phase particles in the multiphase system is 50 wt % or less.

Figure 1:
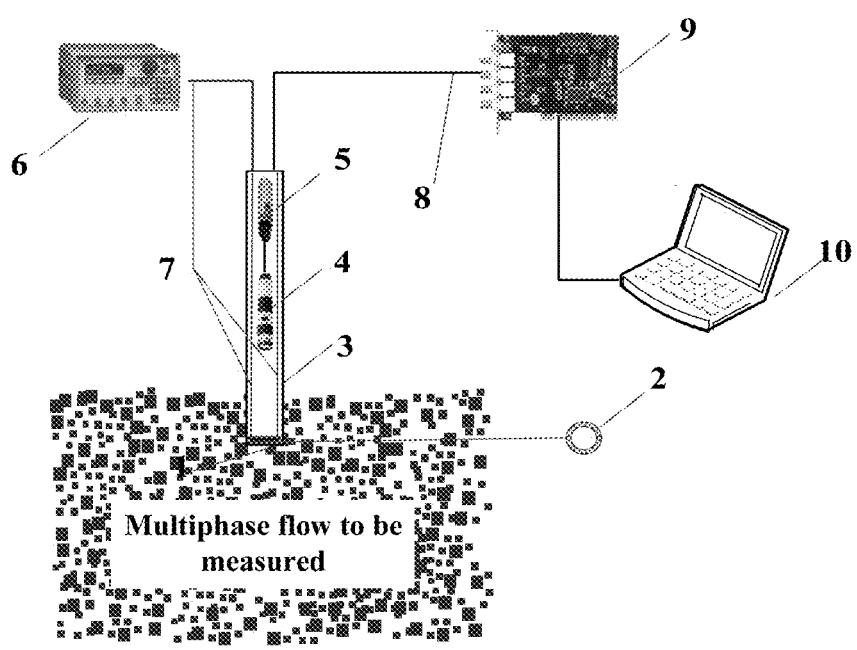
FIG. 1 is a schematic diagram illustrating the structure of an immersive online multiphase measuring instrument provided by Example 1.

Example 1: Acquiring Image of Dispersed Phase in Gas-Liquid System by Utilizing Immersive Online Multiphase Measuring Instrument The immersive online multiphase measuring instrument, as shown in FIG. 1, includes:

a stainless-steel packaging pipe 3;

a window 1 connected to one end of the stainless-steel packaging pipe 3 in a sealing manner;

an illuminating system for illuminating a multiphase flow, including LED lamps 2 and a modulating light source connected with the LED lamps 2, wherein the modulating light source includes a power supply, a signal generator and an oscilloscope;

a photographic system for photographing, including a telecentric lens 4 and an image sensor which is a miniature high-speed CMOS camera 5;

a controller connected with the signal generator and the image sensor;

a signal processing and output system connected with the image sensor; and a display system connected with the signal processing and output system, wherein the LED lamps, the telecentric lens and the image sensor are positioned in the stainless-steel packaging pipe, and the modulating light source, the controller, the signal processing and output system and the display system are positioned outside the stainless-steel packaging pipe; and the controller controls an exposure period of the image sensor to be shorter than a pulse period of the signal generator.

The signal processing and output system, the controller and the display system are integrated into a sampling computer 10.

Specifically, the window 1 is arranged at the most front end of the stainless-steel packaging pipe 3, and is round sapphire glass with an inner side plated with an antireflection film; 20 high-luminosity LED lamps 2 are uniformly distributed behind the window 1, form a ring shape and are uniformly distributed; the telecentric lens 4 is arranged at the rear end of the LED lamps 2, and related parameters of the telecentric lens include: magnification is 1, vision fields of an object and image are respectively ϕ8 mm (ϕ is diameter), a working distance is 250 mm±3%, the telecentricity is less than 0.1 degree, a depth of field is 2.1 mm, a resolution is 14.3 μm, optical distortion is less than 0.12%. For clear imaging, the distance from the front end of the telecentric lens 4 to a surface of an outer side of the window 1 is the working distance of the telecentric lens. The telecentric lens 4 is connected with the miniature high-speed CMOS camera 5 by a standard C port, and parameters of the CMOS camera include: a resolution is 1280×1024, colors are black and white, a frame rate is 150 fps, and an interface is USB3.0. The window 1, the LED lamps 2, the telecentric lens 4 and the miniature high-speed CMOS camera 5 are packaged in the stainless-steel packaging pipe 3. A modulating light source 6 is configured outside the online multiphase measuring instrument, and is connected with the LED lamps 2 by a wire 7. The telecentric lens 4 is connected with a sampling computer 10 provided with a high-speed image acquisition card 9 by a USB3.0 data transmission line 8.

In order to obtain clear images, a control mode shown in FIG. 2 is adopted to realize the synchronization of illumination flashing and CMOS photographing and the control mode is as follows: a switch of a light source is turned on; the intensity and a period of pulse light are set by a light source driver; the exposure time, light balance, frame frequency and gain of image shooting are set by the controller on a computer to match the pulse period of an illuminating signal with the exposure time of the image sensor (the exposure period of the image sensor is shorter than the pulse period of the signal generator) so as to realize the synchronization of pulse light and image shooting.

Image acquisition is carried out in a square organic glass stirring groove with a length T of 0.17 m, a width T of 0.17 m and a height H of 0.23 m, and the stirring speed is 200 rpm. The height H of a static liquid level is equal to T, a stirring paddle is a Rushton paddle, a diameter D of the paddle is equal to T/3, 4 blocking plates are uniformly distributed around the stirring groove, and a width B of each blocking plate is equal to T/10. The length t, width t and height z (same as the coordinate system of the square organic glass stirring groove) of the measured point are respectively equal to 0.05 m, 0.05 m and 0.14 m. Gas is fed by a sintering ceramic hole distributor and the ventilation volume is 120 L/h.

The immersive online multiphase measuring instrument is utilized for acquiring images of the dispersed-phase particles in the gas-liquid system respectively under the following illuminating conditions:

(1) Under the condition that only front light irradiation is provided, the secondary exposure image at the measured point is acquired to obtain an image, as shown in FIG. 3.

(2) Under the condition that the front light and back light are provided, the secondary exposure image at the measured point is acquired to obtain an image, as shown in FIG. 4.

(3) Under the condition that the front light and the reflecting board are provided, the secondary exposure image at the measured point is acquired to obtain an image, as shown in FIG. 5.

(4) Under the condition that the front light and silicon dioxide particles are provided, an image at the measured point is acquired to obtain an image, as shown in FIG. 6.

(5) Under the condition that the front light and aluminum oxide particles are provided, an image at the measured point is acquired to obtain an image, as shown in FIG. 7.

(6) Under the condition that the front light and titanium dioxide particles are provided, an image at the measured point is acquired to obtain an image, as shown in FIG. 8.

Properties of the additive particles added in (4), (5) and (6) are shown in the following Table 1.

TABLE 1

Physical Property Data of All Additive Particles and Concentrations in Multiphase System

| Type of Particles | Wavelength | refractivity | Color | Particle Size | Concentration |
|---|---|---|---|---|---|
| Aluminum Oxide | 580 nm | 1.76 | White | 0.5-1.5 μm | 5 mg/L |
| Titanium Dioxide | 580 nm | 2.62 | White | 0.5-1.5 μm | 5 mg/L |
| Silicon Dioxide | 580 nm | 1.45 | White | 0.5-1.5 μm | 5 mg/L |

By analysis on the images, it can be discovered that the addition of the reflecting particles actually plays a role in improving luminosity of the dispersed phase and the continuous phase in the flow field and the effect is best after the addition of the titanium dioxide particles.

In addition, the particle sizes of all the additive particles in (4), (5) and (6) are adjusted to be any value between 100 nm and 10 μm, such as 150 nm, 200 nm, 230 nm, 280 nm, 310 nm, 400 nm, 500 nm, 800 nm, 900 nm, 1 μm, 3 μm, 5 μm, 8 μm or 9 μm and the like; images at measured points are acquired, and bubble images with high resolution can be still obtained.

The concentrations of all the additive particles in (4), (5) and (6) in the multiphase system are adjusted to be any value between 5 mg/L and 7 mg/L, such as 5.1 mg/L, 5.2 mg/L, 5.3 mg/L, 5.5 mg/L, 5.8 mg/L, 6.2 mg/L, 6.5 mg/L, 6.8 mg/L or 6.9 mg/L and the like; images at measured points are acquired, and bubble images with high resolution can be still obtained.

Example 2: Measuring Change Conditions of Viscosity, Density and Surface Tension of Continuous Phase Before and After Addition of Reflecting Particles Under the experimental conditions of (5) in Example 1, the change conditions of viscosity, density and surface tension before and after addition of the titanium dioxide particles are measured, as shown in Table 2.

TABLE 2

Changes of Physical Properties of Continuous Phase before and after Addition of Titanium Dioxide

| Types | Concentration | Density (g/cm$^3$) | Viscosity (mpa · s) | Surface Tension (Average) mN/m |
|---|---|---|---|---|
| Water | — | 1.00220 | 0.8971 | 71.64 |
| TiO$_2$ | 5 mg/L | 1.00249 | 0.9294 | 71.95 |

According to data analysis of the above table, picture photographing requirement can be met only by a small quantity of titanium dioxide, and the properties of the continuous phase are almost unchanged (all the errors are less than 5%).

Example 3

The following experiments are carried out respectively in the stirring groove provided in Example 1:

(1) The rotating speed of the stirring paddle is 0 rpm, the ventilation volume is 80 L/h; the length t, the width t and the height z (same as the coordinate system of the square organic glass stirring groove) at the measured point are respectively 0.05 m, 0.05 m and 0.14 m; contrast experiments are conducted respectively under the conditions of back brightening, addition of reflecting board and addition of titanium dioxide (with a concentration of 5 mg/L) shown in Table 2 in a water-air system; particle size distribution at the measured point is acquired; and measurement results are shown in FIG. 9a.

(2) The rotating speed of the stirring paddle is 200 rpm, the ventilation volume is 80 L/h; the length t, the width t and the height z at the measured point are respectively 0.05 m, 0.05 m and 0.14 m; contrast experiments are conducted respectively under the conditions of back brightening, addition of reflecting board and addition of titanium dioxide (with a concentration of 5 mg/L) shown in Table 2 in a water-air system; particle size distribution at the measured point is acquired; and measurement results are shown in FIG. 9b.

(3) The rotating speed of the stirring paddle is 0 rpm, the ventilation volume is 120 L/h; the length t, the width t and the height z (same as the coordinate system of the square organic glass stirring groove) at the measured point are respectively 0.05 m, 0.05 m and 0.14 m; contrast experiments are conducted respectively under the conditions of back brightening, addition of reflecting board and addition of titanium dioxide (with a concentration of 5 mg/L) shown in Table 2 in a water-air system; particle size distribution at the measured point is acquired; and measurement results are shown in FIG. 9c.

(4) The rotating speed of the stirring paddle is 200 rpm; the ventilation volume is 120 L/h; the length t, the width t and the height z (same as the coordinate system of the square organic glass stirring groove) at the measured point are respectively 0.05 m, 0.05 m and 0.14 m; contrast experiments are conducted respectively under the conditions of back brightening, addition of reflecting board and addition of titanium dioxide (with a concentration of 5 mg/L) shown in Table 2 in a water-air system, particle size distribution at the measured point is acquired, and measurement results are shown in FIG. 9d.

It can be seen from FIG. 9a to FIG. 9d that the measurement results of the method of adopting the additive particles in the present invention are more accurate.

The applicant declares that, the above only describes specific embodiments of the present invention, but the protection scope of the present invention is not limited to the above. Those skilled in the art should understand that any modification or replacement which can be easily contemplated by those skilled in the art within the technical scope disclosed by the present invention is included in the protection scope and disclosure scope of the present invention.

What is claimed is:

1. A method for improving an identification degree of low-luminosity dispersed-phase particles in a multiphase system, comprising: adding additive particles into a multiphase system containing low-luminosity dispersed-phase particles before photographing the multiphase system to obtain an image including the low-luminosity dispersed-phase particles, wherein the refractivity of the additive particles is greater than that of the low-luminosity dispersed-phase particles, and wherein the low-luminosity dispersed-phase particles are particles with a refractivity that meets the following conditions: the real part is less than 1.5, and the imaginary part is more than 0.5.

2. The method according to claim 1, wherein the method further comprises: carrying out analysis processing on the image of the low-luminosity dispersed-phase particles to obtain parameters of particle size, concentration or speed of the dispersed-phase particles in the multiphase system.

3. The method according to claim 1, wherein the refractivity of the additive particles is 2.0 times or greater that of the low-luminosity dispersed-phase particles.

4. The method according to claim 1, wherein the concentration of the additive particles in the multiphase system is 5 mg/L-7 mg/L.

5. The method according to claim 1, wherein the particle size of the additive particles is 100 nm-10 μm.

6. The method according to claim 1, wherein the color of the additive particles belongs to a bright color system.

7. The method according to claim 1, wherein the color of the additive particles is white.

8. The method according to claim 1, wherein the additive particles are particles with a scattering angle of 90-270 degrees calculated according to the Mie scattering theory.

9. The method according to claim 1, wherein the additive particles are selected from any one or a combination of at least two of titanium dioxide particles, silicon dioxide particles or aluminum oxide particles.

10. The method according to claim 1, wherein the concentration of the low-luminosity dispersed-phase particles in the multiphase system is 50 wt % or less.

11. The method according to claim 1, wherein the low-luminosity dispersed-phase particles are selected from bubbles and/or solid particles.

12. The method according to claim 1, wherein the photographing is immersive photographing.

13. The method according to claim 1, wherein an immersive online multiphase measuring instrument is used for photographing the low-luminosity dispersed-phase particles in the multiphase system.

14. The method according to claim 1, wherein a gas-liquid multiphase system or a liquid-solid multiphase system is used as the multiphase system.

15. The method according to claim 1, wherein the method comprises the following steps: adding white additive particles with a scattering angle of 90-270 degrees calculated according to the Mie scattering theory to a multiphase system containing the low-luminosity dispersed-phase particles before carrying out immersive photographing on the multiphase system to obtain an image including the low-luminosity dispersed-phase particles, wherein the refractivity of the additive particles is 2.0 times or greater that of the low-luminosity dispersed-phase particles, the concentration of the additive particles in the multiphase system is 5 mg/L-7 mg/L, the particle size of the additive particles is 100 nm-10 μm, and the concentration of the low-luminosity dispersed-phase particles in the multiphase system is 50 wt % or less.

* * * * *